United States Patent
Watkins

[11] Patent Number: 5,994,612
[45] Date of Patent: Nov. 30, 1999

[54] POSTOPERATIVE WOUND PROTECTION GARMENT HAVING IMPROVED ELASTICITY, MODULUS AND BREATHABILITY

[76] Inventor: William Bruce Campbell Watkins, 1072 Stovall Ridge Ct., Lawrenceville, Ga. 30043

[21] Appl. No.: 09/127,208

[22] Filed: Jul. 31, 1998

[51] Int. Cl.[6] .............. A61F 13/00; A61L 15/00
[52] U.S. Cl. .................. 602/41; 2/69; 602/75; 128/156
[58] Field of Search ................ 602/41, 42, 44, 602/53, 75, 76, 79; 66/170, 192, 194, 195; 428/193, 192; 442/203, 192, 195, 304, 313, 314; 604/385.1, 394, 389; 2/69

[56] References Cited

U.S. PATENT DOCUMENTS

| | | |
|---|---|---|
| 280,565 | 7/1883 | Bray . |
| 3,713,450 | 1/1973 | Williams ............................ 128/564 |
| 3,752,163 | 8/1973 | Kaplan . |
| 3,934,583 | 1/1976 | Hollingshead et al. ............ 128/165 |
| 4,027,667 | 6/1977 | Swallow et al. .................... 128/165 |
| 4,207,885 | 6/1980 | Hampton et al. ................... 128/156 |
| 4,377,160 | 3/1983 | Romaine ............................ 128/156 |
| 4,424,596 | 1/1984 | Jackson ................................ 2/240 |
| 4,745,917 | 5/1988 | Hasty et al. ........................ 128/165 |
| 4,753,231 | 6/1988 | Lang ..................................... 128/56 |
| 4,820,296 | 4/1989 | Masliyah ........................... 604/385.1 |
| 4,909,049 | 3/1990 | Baesgen et al. ...................... 66/195 |
| 4,961,418 | 10/1990 | McLaurin-Smith ................ 128/157 |
| 4,984,584 | 1/1991 | Hansen et al. ..................... 128/898 |
| 5,054,129 | 10/1991 | Baehr .................................. 2/409 |
| 5,120,325 | 6/1992 | Dow, Jr. ............................. 604/304 |
| 5,152,741 | 10/1992 | Farino ................................ 602/79 |
| 5,188,103 | 2/1993 | Smith ................................ 128/380 |
| 5,259,397 | 11/1993 | McCabe ............................ 128/897 |
| 5,265,445 | 11/1993 | Shytles et al. ........................ 66/2 |
| 5,277,700 | 1/1994 | Smith ................................ 602/74 |
| 5,352,216 | 10/1994 | Shiono et al. ..................... 604/312 |
| 5,368,553 | 11/1994 | Newman ............................ 602/58 |
| 5,382,466 | 1/1995 | Ingham .............................. 428/219 |
| 5,425,702 | 6/1995 | Carn et al. .......................... 602/62 |
| 5,429,593 | 7/1995 | Matory .............................. 602/79 |
| 5,449,341 | 9/1995 | Harris ................................ 602/63 |
| 5,497,513 | 3/1996 | Arabeyre et al. .................... 2/240 |
| 5,522,794 | 6/1996 | Ewall ................................. 602/41 |
| 5,527,270 | 6/1996 | Chase et al. ....................... 602/41 |
| 5,632,526 | 5/1997 | McLarty, III et al. ......... 297/452.64 |
| 5,749,843 | 5/1998 | Miller ............................... 602/75 |

*Primary Examiner*—John J. Calvert
*Assistant Examiner*—Robert H. Muromoto, Jr.
*Attorney, Agent, or Firm*—Bernstein & Associates, P.C.

[57] ABSTRACT

A postoperative garment for protection and improved healing of a wound, injury or disease site comprising a first panel and a second panel, the panels being constructed of a fabric structure comprising a blend of at least one polyester fiber and at least one elastic fiber. The fabric has an elasticity of about 200–220+/−10% in both the warp direction and in the fill direction, the difference between the warp and fill direction elasticity preferably being no more than about 3% to about 5%, a compression modulus of about 1 to about 4, and a breathability measurement of 70–100% moisture loss within 30 minutes and an approximate skin surface temperature reduction of about 4–6° F. within about 3–7 minutes as measured by evaporative cooling, and the panels being attachable to each other along one edge by a closure means, such as mated hook and loop fasteners. The improved universal compression characteristics, breathability and thermoregulation provide enhanced ability to promote healing and protect the wound site.

9 Claims, 2 Drawing Sheets

| SAMPLE # | LOT # | MILL # | MACHINE # | ROLL # | CUT # | WIDTH (INCHES) | WARP TENSION 20% | 30% | 50% | WARP STRETCH | SIDE TENSION 20% | 30% | 50% | SIDE STRETCH |
|---|---|---|---|---|---|---|---|---|---|---|---|---|---|---|
| 1A | 4829 | | 11 | 0887 | 3 | 74 | 3.48 (50%) | | | 202 | 1.96 (50%) | | | 207 |
| 1B | | | | | | | 3.37 | 4.58 | 6.68 | 192 | 1.17 | 1.88 | 3.51 | 199 |
| 1C | | | | | | | .75 | 2.04 | 3.66 | 200 | .65 | 1.07 | 2.06 | 204 |
| 2A | 1291 | 08 | 064 | 0511 | 3 | 74.5 | 3.04 (40%) | 4.42 (60%) | 5.30 (80%) | 182 | 2.03 (40%) | 6.17 (80%) | | 169 |
| 2B | | | | | | | 2.81 | 3.91 | 5.91 | 189 | 1.98 | 3.57 | 6.88 | 179 |
| 2C | | | | | | | 1.29 | 2.19 | 3.63 | 189 | .61 | 1.23 | 3.12 | 182 |
| 3A | 2081 | 08 | 127 | 0379 | 3 | 43.75 | 1.42 (40%) | 2.18 (60%) | 2.84 (80%) | 232 | 3.13 (40%) | 7.58 (80%) | | 142 |
| 3B | | | | | | | 2.24 | 3.10 | 4.41 | 236 | 4.07 | 6.61 | 10.24 | 147 |
| 3C | | | | | | | 0.37 | 0.95 | 1.81 | 245 | 0.66 | 1.64 | 4.23 | 156 |

FIG. 4

POSTOPERATIVE WOUND PROTECTION GARMENT HAVING IMPROVED ELASTICITY, MODULUS AND BREATHABILITY

FIELD OF THE INVENTION

The present invention relates to postoperative wound site and injury recovery garments and more particularly to garments made of a polyester fiber material and an elastic fiber material, using a fabric structure having improved elasticity, compression, breathability and thermoregulation characteristics.

BACKGROUND OF THE ART

Wound and injury healing is a complex science affected by many inter-related body functions. Arterial and venous blood flows, lymphatic drainage and body temperature are three of the key factors in the reduction of the time for a wound or injury to heal without complications. Such complications can be life-threatening as well as inhibiting proper wound healing and include edema, seroma, hematoma, and infection, to name a few. Medical professionals address several of these factors with current procedures, but the current art neglects the simultaneous interaction of the previous mentioned blood flows, lymphatic drainage and maintenance of body temperature with wound or injury healing.

Arterial and venous blood flows are intricately related and regulated by the body. Flow pressure ranges are important and remain within certain parameters; changes to them can greatly affect body function as well as wound healing. Arterial pressures normally remain with 120 mm Hg (systolic) and 80 mm Hg (diastolic) and, due to the muscular nature and structure of the body's arterial delivery system, remains relatively constant. On the other hand, venous pressures are more variable because veins are oftentimes compressed and consequently impede blood flow back to the heart. The central venous pressure is normally 0 mm Hg while the venous resistance and the effect of hydrostatic pressure can vary the venous pressure up to 90–100 mm Hg. Key then to the continuous flow of arterial and venous blood flows is the venous pump. The veins are constantly being squeezed and compressed by the body's muscles and other external pressures. It is important to note that the function of the venous system is significantly important to the circulatory filling pressure, an important determinant of cardiac output. The slightest improvement of venous tone and venous filling ultimately will positively affect cardiac output, which can be correlated to as an important factor to improved wound healing. External compression garments have been prescribed as an aid to a reduction in venous flows such as varicose veins and it is a known treatment.

The lymph system is an accessory route used by the body to maintain fluid balance between the interstitial spaces and the blood. Most of the fluid escaping from the capillaries is reabsorbed into the venous capillaries but the remaining 10% is key both to life function and wound healing. The lymph system, with this small amount of fluid, can also carry proteins and particulate matter away from tissue spaces (i.e., a wound site) that would not normally be removed by capillary action. The action of this function of the large vessel lymph system is called the lymphatic pump and is an intricate, fine functioning system of major lymph vessels and valves. Key to this is that the large lymph vessels can be compressed by the walls of the lymphatics themselves or by additional pressures from the surrounding surfaces. This same function in the large vessels occurs in the lymph capillaries. Note that during the normal postoperative period, the patient is restricted from activity, and is sometimes confined to a bed. This quiet period is contraindicated for the lymphatic pump action as there is no additional external factors to increase lymphatic flow during a time that the body most likely has need of such (edema, seroma, hematoma and other complications). An externally applied compression would be helpful and advantageous.

Although mentioned briefly above, the removal of proteins from the interstitial fluid spaces is an important balancing effect. Proteins, in other than proper amounts, can affect tissue colloid osmotic pressures, which can affect capillary fluid absorption and interstitial fluid volumes and pressures. Interstitial fluid pressures are normally negative and are maintained this way by a proper functioning lymphatic pump but even more so by the removal of excess proteins. The area around the postoperative wound site has been most likely traumatized by a number of factors and thus the proper functioning if the wound site has been reduced. External compression can aid the body and more specifically lymphatic flows to maintain protein balances by maintaining the normal "dry" state of the interstitial spaces.

Some common postoperative complications directly relating to interstitial fluid spaces are edema, seroma and hematoma. Many factors can cause the interstitial pressures to increase and without a similar increase in fluid flows, then there is a fluid buildup or edema. A stretch of the tissue spaces occurs with edemas of more than a few days—sometimes even a few hours—so proper and immediate treatment is important. Further to the stretch of the tissue is that fact that this excess fluid disrupts the normal absorption and use of tissue nutrients as the cells are now further from the capillaries. In the case of a wound site, this will slow the recuperative capacities of the body to heal the wound. Seromas can also affect the wound or injury site as does edema but, additionally, the danger of infection is increased. A hematoma similarly affects the wound site. However, it is possible to proactively address the possibility of edemas, seromas, and hematomas by applying external pressure immediately postoperatively with the intent of increasing capillary pressures and lymphatic flows possibly with a target of 17 mm Hg above the normal capillary pressure. This can be done with a properly designed compression garment.

It should be noted that arterial, venous and lymphatic pressures and flows are intricately balanced and interrelated. Additionally, the interstitial fluid volume and pressures are also balanced with these systems. The skin acts as the body's normal enclosure and it has its own elastic characteristics. Injury or wounds may disrupt the normal fluid and pressure balances causing fluids to build up and the skin stretches or contracts depending on the time from injury. Elastic bandaging has been used for many years as an indication in some of these cases, but not widely so as there are well-known cases of the application of conventional elastic bandages or other dressings that due to their design, material composition or application actually worsened the patient condition and caused complications. The correct application of compression is critical and should be able to perform within the intricate requirements of the body's systems. A fabric that could perform as good or better than skin, in stretch, compression, and thermoregulation, would be a great asset to the patient's postoperative regime.

Blood flows are directly affected by the body's autonomic response to maintain the body's core temperature of 37° C. within about 0.6° C. Core body temperature varies depending on external and internal influences, but is much more stable than the body's surface temperature. Heat is produced continually by the body during its metabolic processes and this heat is naturally lost to the surroundings through various mechanisms, principally radiation, conduction, evaporation and air convection. These processes are dynamic and interrelated. The skin is the key organ that is used by the body to maintain temperature and blood flow to the skin's venous plexus and can be up to 30% of cardiac output. Circulation of the skin has two main (and sometimes conflicting functions): 1) nutrition of the skin and 2) conduction of body heat. The rate of blood flow through the skin is the most variable of any other part of the body because the flow to regulate the temperature of the body is affected by the body's momentary metabolic rate and its immediate surroundings. The sympathetic nervous system automatically responds to these internal and environmental factors to vasoconstrict or vasodilate the skin's blood vessels and begin the perspiration process. For example, blood flow to the skin can increase up to 7 times its normal flow if the body needs to cool itself; this is a significant drain on cardiac output requiring blood to be redirected away from other needed body sites (such as a healing wound). Additionally, if the body is cool, then vasoconstriction of the skin occurs and blood flow is redirected to internal core organs and functions (and possibly away from a wound site). There is then a constant conflicting need for blood flow due to the body's need for temperature regulation and tissue nutrition, which can be contrary to the indications for proper wound site healing.

The clothing or in the case of wound sites, the dressings, placed on top of or proximate to the skin directly affect the results of the aforementioned heat-maintaining processes. Their breathability and thermoregulation characteristics influence their effect on the body. Clothing can trap air next to the skin and thus reduce the effect of the convective movement of air against the skin. The radiative effect of the skin is reduced as the clothing can reflect this heat back to the skin reheating it. Finally, perspiration is only effective as a cooling mechanism if it can evaporate; dripping perspiration is lost body energy that could have been directed toward wound healing. First, the clothing must be efficient in wicking moisture away from the skin. In so doing it becomes wet and must be able to maintain body temperature even when wet; many fabrics increase the body's heat loss by 20–30 times when filled with moisture. Clothing that absorbs moisture but does not evaporate effectively in essence reduces the effectiveness of the body's sweating mechanism. Additionally, patient comfort directly affects patient compliance. Since tapes, elastics, and commonly used postoperative and post-injury garments can be noticeably uncomfortable, it is not uncommon for a patient to self-direct the removal of a wound site dressing much earlier than their postoperative instructions to the detriment of their postoperative result. It would be desirable to have an interactive performance fabric that can aid the body in maintaining core body temperature amidst a variety of external environments and keep the skin dry would aid the body in maintaining internal blood flows (to a wound site) for tissue nutrition purposes rather than temperature maintenance.

The wound site is changing over the time of the postoperative period. The wound or injury site postoperative condition is significantly different 24 hours following injury or surgery than it is two or three weeks following surgery. In the cases of some injuries (such as burns), postoperative treatments are often indicated for more than one or two years. Today, patients are treated with singular, stand alone dressings or the medical professional simply modifies standard tapes and elastics to formulate a dressing for the patient's then current condition. No series of specifically designed garments is used although the wound site and the patients' conditions are dynamically changing.

Current garments, bandages, elastics and dressings are constructed of fabrics commercially available. Both the concepts of stretch fabric and elastic garments are nothing new in themselves and are commercially available in many types. Fabrics that absorb moisture are also not new. Most of these stretch fabrics are now manufactured of a spandex material like LYCRA® (a registered trademark of E. I. DuPont de Nemours & Co.). Spandex is a complex, synthetic, elastomeric material with stretch up to 500–600% and is not practical in solely being used to make garments. It is blended with many other types of fibers such as polyesters, cottons, nylons and others commercially available.

Along with these different fiber blends, different fabric construction methods can be used such as weaving and knitting. Within knitting, tricot and raschel constructions are used. Additionally, there is another type of commonly used fabric that is constructed of similar fibers but manufactured into a web.

All of these in one form or another have limitations and affect the body or more specifically the wound or injury sire in various ways. The use of many blends of fibers in either woven or knitted fabrics is usually limited in that the stretch (elasticity) and the modulus (compressive power or force) are different in the two orientations of the fabric: warp or length direction and the width or fill direction. Ranges vary widely depending on the fibers used, fiber compositions, and manufacturing method but might typically range between 100–180% for the warp and 70–140% for the filler. Modulus readings also vary widely and can range from 2–4 in the warp and 1–3 in the fill. Fiber compositions using synthetics, usually nylons, offer negligible breathability; nylon does not wick or evaporate moisture effectively. Some polyesters do so and it has been a goal of some fabric manufacturers to develop a family of performance fabrics that are used primarily in sport and outdoor activities. There has been a lack of medically-oriented garments to address the combination of the body's ability to recover from wounds or injuries. No medically oriented garments effectively address the combination of the body's need for uniform compression to aid its fluid and pressure systems and the body's need to maintain its temperature. These two key factors directly affect the body's ability to recover from wounds. And, finally, no discussion has been previously made about the possibility that a particular medical garment used immediate postoperative or post-injury might not be applicable 2–3 weeks later. The medical professional knows this reality and oftentimes prescribes different dressings, but in the case of many post-operative and post-injury regimes, they instruct the patient to buy a non-medical item at a retail store which may be impracticable or ineffective.

Additionally, patients have reported discomfort with conventional garments due to excessive heat and moisture buildup between the skin and fabric, especially during summer months in temperate climates and year round in tropical climates. This discomfort can cause the patient to not use the garment for the full physician-prescribed period of time or worse, cause potential medical complications, including improper or prolonged healing, worse scar formation, improper skin retraction, pain caused by fluid buildup or inflammation, and the like.

None of the current art or available resources to today's medical professional encompass the full range of factors influencing the postoperative or post-injury patient. Accordingly, there is a need for a fabric having desirable breathability yet having uniform and high elasticity measurements. The changing of a wound/injury site over time requires changing treatment options. The ambulatory patient has a need to comfortably function in normal activities whole wearing their postoperative/post-injury dressings while complying with their postoperative and/or post-injury instructions. There is a need for dressings, through uniform compression, to assist the body's natural hemodynamic, venous, and lymphatic systems at various stages of wound site or injury healing. There is a need to maintain full percentage of cardiac output directed to natural tissue nutrition at the wound site while minimizing the body's need to regulate its temperature and redirect blood flows. There is a need to, during the above mentioned temperature maintenance autonomic process, improve the body's sweating (cooling) mechanism to more efficiently use body resources (especially blood flow) to cool/heat the body.

DESCRIPTION OF THE PRIOR ART

U.S. Pat. No. 5,359,732, issued to Waldman et al., discloses a swimsuit including a fabric having a substantially uniform stretch in both the longitudinal and horizontal directions. The fabric also has a high modulus in the horizontal direction of the suit, as compared to the vertical directions, to provide improved retention and camouflage of body parts. Waldman et al. does not address the issue of breathability of the fabric, primarily because the fabric is used as a swimsuit, which is designed to get and stay wet.

U.S. Pat. No. 4,909,049 issued to Baesgen et al., discloses a method for manufacturing a bielastic weft-insertion fabric in which the longitudinal and transverse elastic forces are balanced. The fabric has weft threads of elasthane yarn running transversely of the fabric web which are transformed by means of hooks and the knocking-over and holding-down sinkers into loops which are then incorporated into the ground warp knit fabric of the hard fiber yarn.

SUMMARY OF THE INVENTION

The present invention addresses the deficiencies in the prior art and provides a postoperative and therapeutic garment for protection and improved healing of a wound, injury or disease site. More particularly, the present invention provides a postoperative and therapeutic series of garments comprised of a number of types of designs for various body parts and surgical procedures, different types of closures and attachments, and made of a fabric or series of fabrics that have specific elasticity, modulus, breathability and thermoregulatory characteristics.

In a preferred embodiment, the invention comprises a first panel and possibly a second panel or panels, the panels being constructed of a fabric structure comprising a blend of at least one polyester fiber and at least one elastic fiber, such as Lycra®, such that the fabric has an elasticity of about 200–220+/–10% in both the warp direction and in the fill direction, the difference between the warp and fill direction elasticity being no more than about 3% to about 5%, a compression modulus of about 1 to about 4, and a breathability measurement of 70–100% moisture loss within 30 minutes and an approximate skin surface temperature reduction of about 4–6° F. within about 3–7 minutes as measured by evaporative cooling, the panels being attachable to each other along one edge by a closure means.

The present invention is contemplated to be made of a fabric that will have similar elastic and modulus readings in the warp and fill directions. By having similar elastic properties in the warp and fill directions the fabric will have uniform stretch. This uniform stretch will cause the fabric to enclose the body parts completely and uniformly cause a body molding process similar to that of a "second skin." However, here the present invention further departs from the current art in that the present invention addresses the other component of uniform compression in that the modulus in the warp and fill directions are contemplated to be similar. All other fabrics achieve a degree of compressive force but with different moduluses in the horizontal and vertical directions. Almost all stretch clothing is constructed of cut pieces having the warp direction (almost always the stronger modulus reading) oriented in the horizontal direction of the garment. If equal compressive force is desired, typically a paneled system must be used with one panel being oriented with the warp direction in the garment's horizontal direction and the other panel with the warp in the vertical direction. Even this is a compromise as the compressive force will always be limited to the lowest modulus reading of the paneling system. Additionally, using multi-layered fabric increases both the weight of the total garment and, as is the case with nylon/Lycra fibers, increases the body heat retained by the fabric. To date, prior art has not seen a need to address this deficiency. One of the closest to achieving a better compressive force was Waldman et al., but because they were only interested in body contour control, they were accepting of greater horizontal modulus.

As the ambulatory patient moves into normal activities, the movements will include joint flexion. Movement of the legs, hips, and bending at the waist, for example, effect movement in the body's vertical direction. Hence, there is a vertical component in the effect of clothing on the body. This, for example, is why an above-the-knee exercise short will "ride up" the thighs or a below-the-knee exercise pants can ride up to constrict and apply a "tourniquet-like" effect immediately below the knee. As the clothing is being moved and relocated on the body part, the compressive forces are changing. The garments are sewed using cloth pieces designed from a pattern designed for that body part, i.e., the bottom leg opening of an above-the-knee pair of stretch shorts is designed for the circumference immediately above the knee. If the garment rides up 3–6 inches, then the bottom leg opening might now be positioned at mid-thigh which could represent a difference of 4–8 inches of extra stretch. In the typical fabric, this will effect a significantly different compressive force on the body part and the patient will feel that the garment is "too tight." In the postoperative and post-injury patient, this new level of pressure can immediately affect the pressure balance and flows of the hemodynamic, venous, and lymphatic systems.

Accordingly, it is a principal object of the present invention to support the process normally present in wound and injury healing with garments providing compression, elasticity, breathability and thermoregulation. Compression will support the venous and lymphatic drainage by lowering swelling and preventing complications. This compression will be the result of fabric or fabrics that just like the skin does, have substantially the same elasticity and modulus in both the warp and width directions. This fabric, like a true second skin, will also enhance maintenance of proper body temperature, which will increase nutrition support by arterial vasodilatation. It is another object of this invention to provide a postoperative surgical and post-injury garment having improved breathability which maximizes the efficiency of sweating (better than skin) while still maintaining the above compression characteristics. It is a further object of the present invention to provide a system of at least three garments that addresses the progressively changing requirements of the postoperative wound site of different surgical and postoperative patient applications. Other objects, features and advantages of the present invention will become apparent upon reading the following detailed description of the embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which:

FIG. 4 shows Table 1.

DESCRIPTION OF THE PREFERRED EMBODIMENTS

The present invention provides a postoperative surgical garment for protection of a wound site composed of a fabric constructed with a blend of polyester and Lycra® fibers. The polyester is a cationic dyeable polyester, and may be a continuous filament yarn. The yarn can have a tetrachannel cross section, or other cross sections as are known to those of ordinary skill in the art.

Figure 3:
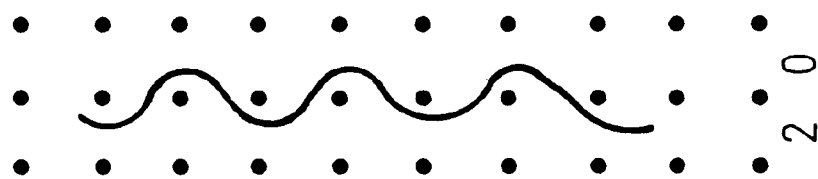
FIG. 3 is a schematic view of the back bar.
Figure 2:
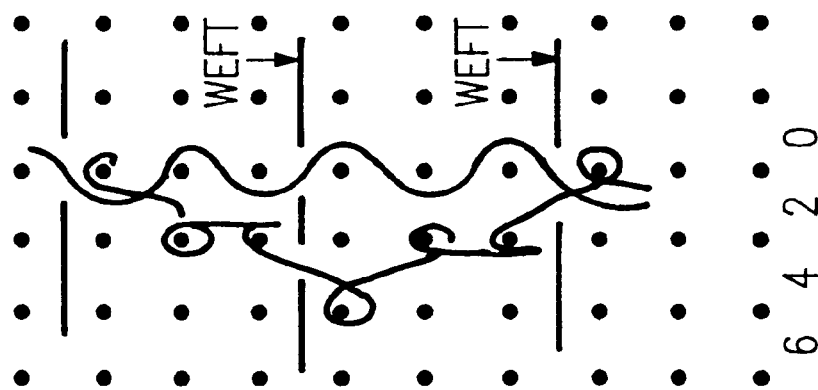
FIG. 2 is a schematic view of the middle weft insertion.
Figure 1:
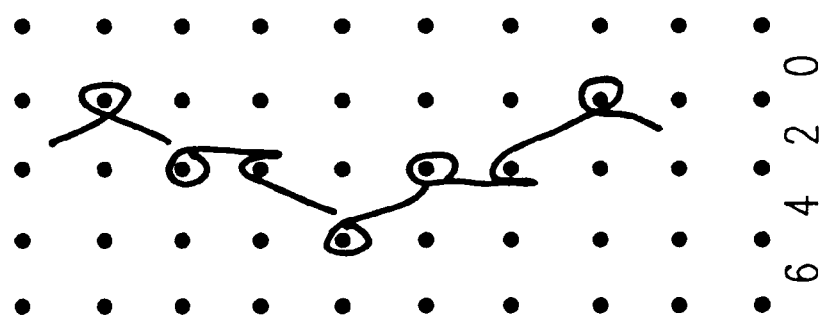
FIG. 1 is a schematic view of the front bar of a fabric according to the present invention.

A preferred fabric is manufactured as a proprietary composition by Liberty Fabrics (New York, N.Y.) commercially available as CoolMax™ WeftLoc™ under the designation 2175 and 9617. WeftLoc™ fabric is comprised of elastomeric fibers and is produced on a specialized Liba Raschel WeftLoc weft insertion machine using a combination of non-elastic rigid warped yarn, such as polyester or nylon, along with warped spandex elastomeric yarn such as Lycra®. The WeftLoc™ fabric structure is similar to traditional 2-Bar laid in Lycra® Raschel construction with the Lycra® yarn coming from warps through a back grid bar #2 (see FIG. 3) and knitted together with a rigid yarn from a separate warp and front guide bar #1 (see FIG. 1). Additionally, a weft insertion technique is used to introduce into the fabric a weft direction horizontal lay-in of Lycra® elastomeric yarn in such a way as to not enter the hooks of the needles, but rather place the yarn behind and in back of the needles, and so thereby not forming loops. The weft inserted Lycra® yarns then lay in the fabric in a straight line, from selvedge to selvedge, performing like weft yarns in a filling width stretch woven fabric. Both the warped Lycra® and the weft inserted Lycra® are fed into the construction during knitting under extended conditions, thereby upon relaxation and finishing to a contracted state, the resultant product has both warp stretch with modulus and weft stretch with modulus. This fabric forming technique allows for the design of performance stretch fabrics with a generous 200% length×200% width stretch with power and modulus results in both directions. This kind of balanced two-way power stretch cannot be achieved using the traditional warp yarn system along in Raschel fabrication. In this example, the weft is inserted in a 1-in, 2-out arrangement (see FIG. 2), resulting in a square opening mesh which avails itself as the fabric is stretched and extended.

The fabric can be manufactured to have a range of elongation, modulus and breathability characteristics, depending on the fiber component composition used. In order to alter breathability, a chemical treatment can be added to the fabric during finishing, which treatments are known to those skilled in the art and are commercially available. The postoperative and therapeutic garments of the present invention are typically used after plastic, aesthetic, reconstructive, and orthopedic surgery, as well as post-burn recovery although these uses could be easily expanded into other applications.

The fabric is cut, seamed and joined to produce any of a number of possible shapes or designs, including, but not limited to, male or female girdles, abdominal binders, surgical brassieres, face masks, vests, sleeves, leotards, gloves, body suits, leg stockings, and the like. The particular garment shape used is determined by the wound site location and body contours. Typically, the garment will be composed of a first panel and possibly a second panel of the fabric, which are joined together. Depending on the shape, an opening and closing fastener system is utilized to close the garment, such as, but not limited to, mated hook and loop fasteners, zippers, hook and eye closures, snaps, buttons, and the like. Lace edging or a waist band can be stitched onto ends of the fabric for enhanced comfort an aesthetic appeal. The lace edging can be backed with a ribbon of silicone, typically flat in shape, to prevent the garment from sliding up the user's leg. To vertically position the abdominal and back part of the garment, vertical supports such as plastic supports, staves, bones, suspenders, waist elastics, or the like, in the abdominal and back sections are used.

Optionally, a surgical drain, e.g., a tube, can be incorporated into the garment via an aperture formed in the fabric, through which the drain is inserted. The drain facilitates passage of fluids, e.g., wound exudate, from the wound site.

An important feature of present invention is that the garment have substantially the same elongation, within approximately 3–5%, in both the warp and width directions to accommodate the fact that skin stretches universally the same in all directions. Uneven compression can result in distorted wound healing and scar formation, as well as uneven distribution of fluids around the wound site. The fabric used in the present invention preferably has a compression modulus of from about 1 to about 4 pounds, more preferably of from about 3 to about 4 pounds. Alternatively expressed, the modulus is from about 7 to about 25 mm Hg.

Another important feature of the present invention is that the stretch coefficient of the fabric be substantially the same in both directions. In a preferred embodiment, the stretch coefficient (elasticity) is 200–220%±10% in the warp direction and 200–220%±10% in the width direction. Most garments have fabrics designed to stretch more in one direction than the other direction, typically 120–180% in length and 70–120% in width.

Another important feature of the present invention is that the fabric have high breathability. When a postoperative surgical garment is worn continuously, moisture and heat buildup can cause discomfort, itching, skin rash, retard proper healing and potentially cause medical complications. Prior art garments have been made of fabric, such as nylon or nylon blends, which have poor or marginal breathability, most likely to maintain compression or stretch characteristics. The present invention incorporates a fabric having desirable compression modulus and strength coefficient, but maintains high breathability measured as 70–100% moisture loss within 30 minutes and an approximate skin surface temperature reduction of about 4–6° F. within about 3–7 minutes as measured by evaporative cooling. The garment of the present invention has high wicking characteristics so that moisture produced by the body is wicked away from the skin, through the fabric and evaporates on contact with ambient air.

Another aspect of the present invention provides a system of postoperative surgical garments, used sequentially, each garment in the system having specific structural characteristics. As the wound heals less compression is required. Also, as less compression is required, a different closure or fastener may be used for increased comfort. The system of the present invention uses a plurality of garments. Each garment may incorporate the polyester/Lycra® fabric described hereinabove. For each garment, differences in compression modulus are achieved by altering the concentrations of the individual fiber components or by varying the cut and shape of the garments.

A first stage garment has medium compression modulus, in the range of from about 7 to about 17 mm Hg as measured by a HATRA machine, as is known to those skilled in the art. The first stage garment also has very easily manipulated closure means, such as VELCRO®, since the garment may need to be opened or removed frequently to change the dressing or clean or observe the wound site. Preferably, the first stage garment is colored using a dye or other coloring means to be conducive to (i.e., blend in) postoperative wound characteristics. This is desirable because typically there is discoloration of wound site dressings due to blood and other body fluid discharge. A darker garment can make the patient more comfortable aesthetically in that the do not see the normal fluid discharge.

The first stage garment is worn immediately after surgery to about the third day thereafter. It is to be understood that for each stage garment the range of wearing time can vary, depending on the individual, the surgical or operative procedure, and the instructions of the prescribing physician. By "wearing time" it is meant that time period which a particular type of garment will be worn, and is not meant to indicate that the garment is never to be taken off during that time. Indeed, if there is substantial bleeding or wound exudate that soils the garment, it should be cleaned or changed frequently to prevent infection or inflammation.

A second stage garment has medium to high compression, in the range of from about 10 to about 25 mm Hg. A preferred fiber composition uses polyesters available from E. I. duPont de Nemours & Co. (Wilmington, Del.) commercially available and sold under the designation 50/34 T929. The Lycra® is available under the designation 140 T127 and 280 T127. The garment has easy entry/exit closure means, such as a zipper and/or hook and eye closures, and is more functional on a daily basis. The second stage garment is designed to be similar in appearance to top intimate wear in color and trim. It is worn from about the third day postoperative to about three to eight weeks.

A third stage garment has low to medium compression, in the range of from about 7 to about 17 mm Hg, and is used mainly for support. The fiber composition may be the same as that of the second stage garment.

The novel system of a set of sequentially used garments incorporating the above described fabric provides enhanced patient comfort and will improve the likelihood of use by a patient for the full prescribed period. Breathability is improved, which also enhances patient comfort, increases wearer tolerance time and compliance, and thus reducing overall postoperative wearing time.

The invention will be further described in connection with the following examples, which are set forth for purposes of illustration only. Parts and percentages appearing in such examples are by weight unless otherwise stipulated.

EXAMPLES

Example 1

Fabric style number 96175. The fabric was knitted from:

| | |
|---|---|
| 68% | 50/34 T929 Cat Dye CoolMax ™ polyester |
| 8% | 140 T127 Dull Lycra ® |
| 24% | 280 T127 Dull Lycra ® |

CoolMax™ is a cationic dyeable, polyester yarn that is spun in a dog bone cross section which provides channels to permit moisture movement along the fibers. The fabric had a warp stretch of 220%+/−10% and a width stretch of 220+/−10%. Both stretch measurements were taken under a load of 30 pounds using a Zwick apparatus, as is known and available in the art. The modulus in the warp direction was 50% 3.25+/−0.33, and in the width direction was 50% 1.45+/−0.15. The fabric weight was 8.95 ounces per square yard (osy). The fabric was cut, edge seamed and stitched into several possible garment styles using a closure made of hook and eye, Velcro® type hook and loop, zipper, etc., depending on the garment style.

Example 2

Style 96175, Dyelot #Z-0393. The fabric was knitted from:

| | |
|---|---|
| 68% | 50 denier CoolMax ™ polyester |
| 8% | 140 denier T127 Dull Lycra ® |
| 24% | 280 denier T127 Dull Lycra ® |

The fabric had a warp stretch of 210+/−10% and a width stretch of 226+/−10%, both measurements taken under a load of 30 pounds using a Zwick apparatus. The modulus range was 1–4 at 50% stretch with 200 warp/210 width stretch at 30 lbs. on a Zwick machine. The weight was 8.95 oz/yd2. The fabric was cut, edge seamed and stitched into a number of possible garment styles using a closure made of hook and eye, Velcro®, zipper, etc., depending on the garment style.

Example 3

| |
|---|
| Style 2175 |

The yarn construction is 8% 140 denier T127 Lycra®, 23% 280 denier T127 Lycra®, and 69% 50 denier nylon. The modulus range was 2–4 at 60/30% stretch with 200 warp/200 width stretch at 30 lbs. on a Zwick machine. The weight was 8.40 oz/yd.

EXPERIMENTAL RESULTS

TABLE 1 in Fig. 4 shows experimental results of several trials.
Key to sample identification

| Sample | Material |
|---|---|
| 1A | The standard for present invention (polyester Lycra) |
| 1B | 1A under 30 pound tension at the first cycle |
| 1C | 1A under 30 pound tension at the third cycle |
| 2A | The standard for Style 94158 (nylon Lycra) |
| 2B | 2A under 30 pound tension at the first cycle |
| 2C | 2A under 30 pound tension at the third cycle |
| 3A | The standard for Liberty PowerLycra 90357 (nylon Lycra) |
| 3B | 3A under 30 pound tension at the first cycle |
| 3C | 3A under 30 pound tension at the third cycle |

For Sample 1B (after the first stretch cycle) the warp stretch was 192 and the side stretch was 199; both numbers are relatively high and similar to each other, indicating desirable stretch in both directions, and the stretches being roughly equivalent, producing a fabric having uniform stretch. For Sample 1C (after the third stretch cycle) the warp stretch was 200 and the side stretch was 204, also showing uniform and good stretch.

Sample 2B (after the first stretch cycle) had a warp stretch of 189 and a side stretch of 179. Both numbers are lower than desirable (200 is a desirable goal), and the numbers indicate a greater difference in stretch than is desirable.

Sample 2C (after the third stretch cycle) had a warp stretch of 189 and a side stretch of 182, similar to Sample 2B.

Sample 3B (after the first stretch cycle) had a warp stretch of 236 and a side stretch of 147, indicating very good warp stretch, poor side stretch, and poor stretch uniformity.

Sample 3C (after the third stretch cycle) had a warp stretch of 245 and a side stretch of 156, similar in performance to Sample 3B.

As the data indicates, the fabric of the present invention (Samples 1A–C) provides desirable levels of stretch in both warp and side directions, and relatively uniform stretch in both directions.

While the invention has been described in connection with certain preferred embodiments, it is not intended to limit the scope of the invention to the particular forms set forth but, on the contrary, it is intended to cover such alternatives, modifications, and equivalents as may be included within the spirit and scope of the invention as defined by the appended claims.

What is claimed is:

1. A postoperative garment for protection and improved healing of a wound, injury or disease site, comprising: a first panel and a second panel, said panels being constructed of a fabric structure having warp and fill directions with at least one elastic fiber and a blend of at least one selected from a group consisting of polyester and nylon fiber such that said fabric has an elasticity of about 200–220+/−10% in both the warp direction and in the fill direction, the difference between the warp and fill direction elasticity being no more than about 3% to about 5%, a compression modulus of about 1 to about 4, and a breathability measurement of 70–100% moisture loss within 30 minutes and an approximate skin surface temperature reduction of about 4–6° F. within about 3–7 minutes as measured by evaporative cooling, said panels being attachable to each other along one edge by a closure means.

2. The garment of claim 1, wherein said polyester is selected from a group consisting of cationic dyeable polyester, and a continuous filament yarn.

3. The garment of claim 1, wherein said polyester comprises a cationic dyeable, hollow core, continuous filament yarn with an approximate 20% void in fiber interior.

4. The garment of claim 3, wherein said continuous filament yarn has a tetrachannel cross section.

5. The garment of claim 1, wherein said elastic fiber is composed of a synthetic elastomeric material.

6. The garment of claim 1, wherein said garment has substantially equal compressive force in the warp and fill directions.

7. The garment of claim 6, wherein said compressive force is from about 7 to about 25 mmHg.

8. The garment of claim 1, wherein said closure means is selected from a group consisting of mated hook and loop fasteners, zippers, hook and eye closures, snaps, and buttons.

9. The garment of claim 1, further comprising a surgical drain attached to said garment for permitting passage of fluids there through.

* * * * *